United States Patent
Lentz

(10) Patent No.: US 6,796,979 B2
(45) Date of Patent: Sep. 28, 2004

(54) COAXIAL CATHETER SYSTEM FOR PERFORMING A SINGLE STEP CRYOABLATION

(75) Inventor: David J. Lentz, La Jolla, CA (US)

(73) Assignee: Cryocor, Inc., San Diego, CA (US)

( * ) Notice: Subject to any disclaimer, the term of this patent is extended or adjusted under 35 U.S.C. 154(b) by 96 days.

(21) Appl. No.: 10/317,844

(22) Filed: Dec. 11, 2002

(65) Prior Publication Data

US 2004/0116916 A1 Jun. 17, 2004

(51) Int. Cl.⁷ .............................................. A61B 18/18
(52) U.S. Cl. .......................................... 606/21; 606/23
(58) Field of Search ..................... 606/20–26

(56) References Cited

U.S. PATENT DOCUMENTS

| | | | |
|---|---|---|---|
| 4,838,268 A | 6/1989 | Keith | |
| 5,147,355 A | 9/1992 | Friedman | |
| 5,209,727 A | 5/1993 | Radisch | |
| 5,490,859 A | 2/1996 | Mische | |
| 5,516,336 A | 5/1996 | McInnes | |
| 5,868,735 A | * 2/1999 | Lafontaine | 606/21 |
| 5,971,979 A | * 10/1999 | Joye et al. | 606/21 |
| 6,012,457 A | 1/2000 | Lesch | |
| 6,024,740 A | 2/2000 | Lesch | |
| 6,149,574 A | 11/2000 | Trauthen | |
| 6,237,355 B1 | 5/2001 | Li | |
| 6,245,064 B1 | 6/2001 | Lesh | |
| 6,562,030 B1 | 5/2003 | Abboud et al. | |
| 6,569,158 B1 | 5/2003 | Abboud et al. | |
| 6,575,933 B1 | 6/2003 | Wittenberger et al. | |
| 6,575,966 B2 | 6/2003 | Lane et al. | |
| 6,579,287 B2 | 6/2003 | Wittenberger et al. | |
| 6,585,717 B1 | 7/2003 | Wittenberger et al. | |
| 6,589,234 B2 | 7/2003 | Lalonde et al. | |
| 6,592,577 B2 | 7/2003 | Abboud et al. | |
| 6,595,988 B2 | 7/2003 | Wittenberger et al. | |
| 6,602,247 B2 | 8/2003 | Lalonde | |
| 6,629,972 B2 | 10/2003 | Lehmann et al. | |
| 6,635,053 B1 | 10/2003 | Lalonde et al. | |
| 2002/0143323 A1 | * 10/2002 | Johnston et al. | 606/21 |
| 2003/0199861 A1 | * 10/2003 | Lafontaine | 606/21 |

* cited by examiner

*Primary Examiner*—Michael Peffley
(74) *Attorney, Agent, or Firm*—Nydegger & Associates

(57) ABSTRACT

A system for cryoablating target tissue at a treatment site includes an annular shaped balloon attached to the distal end of a first catheter. A cryo-element is attached to the distal end of a second catheter and the second catheter is disposed in the lumen of the first catheter. The cryo-element is positioned at the treatment site using the second catheter. Next, the first catheter is used to advance the balloon over the second catheter to the treatment site where the annular shaped balloon is Interposed between the cryo-element and the target tissue. Saline solution is pumped into the balloon to expand the balloon into contact with the cryo-element and the surrounding target tissue. Next, a refrigerant is expanded to cool the cryo-element, which in turn, freezes the saline solution. The resulting "ice ball" extracts heat from surrounding tissue resulting in the cryoablation of a substantially circumferential portion of tissue.

20 Claims, 3 Drawing Sheets

COAXIAL CATHETER SYSTEM FOR PERFORMING A SINGLE STEP CRYOABLATION

FIELD OF THE INVENTION

The present invention pertains generally to systems and methods for cryoablating internal tissue. More particularly, the present invention pertains to systems and methods for cryoablating conduction blocks to treat patients experiencing heart arrhythmias such as atrial fibrillation. The present invention is particularly, but not exclusively, useful for ablating a substantially circumferentially shaped portion of tissue surrounding the ostium of a pulmonary vein in a single step.

BACKGROUND OF THE INVENTION

Atrial fibrillation is an irregular heart rhythm that adversely affects approximately 2.5 million people in the United States. It is believed that at least one-third of all atrial fibrillation originates near the ostium of the pulmonary veins. Anatomically, two pairs of pulmonary veins are connected to the left atrium of the heart with each pair delivering blood to the heart from one of the patient's lungs. It is further believed that the optimal technique to treat atrial fibrillation is to create circumferential lesions around the ostia where a pulmonary vein connects with the left atrium. More specifically, the goal is to ablate tissue to form a conduction block to thereby prohibit the transmission of Irregular electrical signals that can cause an arrhythmia. To be effective, the conduction block must completely block Irregular signals and this often requires the ablation of a relatively deep, uniform lesion.

Heretofore, due to the relatively large diameters of these ostia, cryoablation procedures have required multiple, successive contacts between the cryo-element and the tissue around the periphery of an ostium. More specifically, these procedures have required the cryo-element to be successively moved around the ostia to create a patchwork array of ablations. This often results In a non-uniform circumferential ablation that fails to form an adequate conduction block. Furthermore, when multiple, successive contacts are prescribed, special catheter structures are generally required to give a catheter the agility required to carefully move from one location to the next within the pulmonary vein. These structures increase the size of the distal end of the catheter, making the catheter harder to steer and navigate through the vasculature of the patient to the treatment site. In short, procedures requiring multiple contacts tend to be complicated, time consuming, difficult to perform, and are generally unreliable.

Another factor that must be considered when ablating internal tissue is the stability of the ablation element (e.g. cryo-element) relative to the target tissue. During ablation, movements of the patient such as heartbeats and breathing can cause the ablation element to move or bounce. Failure to prevent these movements of the ablation element relative to the target tissue can disrupt the flow of energy between the ablation element and the tissue resulting in a non-uniform ablation. As indicated above, non-uniform ablations often result in an ineffective conduction block.

In light of the above, it is an object of the present invention to provide systems and methods suitable for the purposes of cryoablating substantially circumferential ablations of internal tissue in a single step. It is another object of the present invention to provide systems and methods for forming conductive blocks to treat heart arrhythmias such as atrial fibrillation. It is yet another object of the present invention to provide systems and methods for cryoablating internal target tissue that can be performed quickly and are relatively reliable. Still another object of the present invention is to provide systems and methods for cryoablating circumferential ablation that are easy to use or perform and are comparatively cost effective.

SUMMARY OF THE INVENTION

The present invention is directed to a system and method for cryoablating internal target tissue at a treatment site. In one application of the system and method, a substantially circumferential portion of tissue surrounding the ostium of a pulmonary vein is ablated. The resulting lesion functions as a conduction block to treat heart arrhythmias such as atrial fibrillation.

For the present invention, the system includes a balloon that is mounted on the distal end of a balloon catheter. The balloon catheter is elongated and defines a longitudinal axis in the direction of elongation. In more detail, the balloon catheter is tubular shaped and formed with a lumen that extends between the proximal and distal ends of the balloon catheter. The balloon is attached to the distal end of the balloon catheter and placed in fluid communication with the lumen of the balloon catheter. With this combination of structure, a saline solution can be introduced into the balloon by pumping the saline solution into the proximal end of the balloon catheter from an extracorporeal location. In greater structural detail, the balloon has a substantially annular shaped cross-section in a plane substantially orthogonal to the longitudinal axis of the balloon catheter.

The system further includes a cryo-catheter that is disposed within the lumen of the-balloon catheter. The cryo-catheter extends between a distal end and a proximal end and surrounds a lumen for the cryo-catheter. In one implementation, the balloon catheter and cryo-catheter are arranged to be co-axial about the longitudinal axis of the balloon catheter. The system also includes a cryo-element that is mounted on the cryo-catheter at the cryo-catheter's distal end. In one implementation, the cryo-element is formed with an expansion chamber that is placed in fluid communication with the lumen of the cryo-catheter when the cryo-element is mounted on the cryo-catheter.

The cryo-catheter can further include a supply tube that is positioned inside the lumen of the cryo-catheter. In one implementation, the supply tube is positioned inside the lumen of the cryo-catheter to establish a return line between the inner surface of the cryo-catheter and the outer surface of the supply tube. Furthermore, the supply tube can extend from the proximal end to the distal end of the cryo-catheter.

The system further includes a refrigerant supply unit that is positioned at an extracorporeal location to introduce a fluid refrigerant into the proximal end of the supply tube. The fluid refrigerant then traverses through the lumen of the supply tube and exits the supply tube into the expansion chamber of the cryo-element. In one implementation, a flow restricting device such as a capillary tube can be used to restrict flow at the distal end of the supply tube. In this implementation, the fluid refrigerant passes through the restriction and then expands into the chamber to cool the cryo-element. In a particular embodiment of the present invention, a fluid refrigerant is used that transitions from a liquid state to a gaseous state as it expands into the cryo-element chamber. Heat absorbed by the refrigerant during this phase transition (i.e. latent heat) cools the cryo-element.

After expansion, the gaseous fluid refrigerant can pass through the return line and exit the patient at the proximal end of the cryo-catheter.

In operation, the cryo-element is inserted Into the vasculature of the patient and advanced within the vasculature using the cryo-catheter until the cryo-element is positioned at the treatment site, To facilitate positioning of the cryo-element at the treatment site, the distal portion of cryo-catheter can be formed as an articulation segment (see more detailed description below). With the cryo-element in place, the balloon catheter is then used to advance the annular shaped balloon over the cryo-catheter to the treatment site. At the treatment site, the annular shaped balloon is interposed between the cryo-element and the target tissue.

In an alternative implementation of the system, a guidewire can be used to position the cryo-element and balloon at the treatment site. In this implementation, the tip of a guidewire is first inserted into the vasculature of the patient and advanced past the target tissue. Next, an eyelet mounted on the balloon catheter is threaded onto the guidewire and the balloon catheter and cryo-catheter are advanced within the vasculature of the patient until the cryo-element is located at the treatment site. At the treatment site, the annular shaped balloon can be moved relative to the cryo-element to interpose the balloon between the cryo-element and the target tissue.

With the balloon interposed between the cryo-element and the target tissue, saline solution Is pumped into the balloon causing the balloon to expand. More specifically, an inner surface portion of the balloon expands toward the cryo-element and an outer surface portion of the balloon expands toward the target tissue. Filling of the balloon with saline solution is continued until the expanded balloon contacts both the cryo-element and the surrounding target tissue. The shape of the balloon (i.e. the annular shape) allows the balloon to surround the cryo-element and provide a large contact area between the balloon and the cryo-element. The large contact area, in turn, provides for good heat transfer between the saline solution and the cryo-element. In addition, the expanded balloon functions to anchor the cryo-element in place at the site of the target tissue.

Once the balloon has been adequately filled with liquid, the refrigerant supply unit is activated to introduce a fluid refrigerant into the expansion chamber of the cryo-element and thereby cool the cryo-element. In one implementation, nitrous oxide is used as the refrigerant allowing the cryo-element to be cooled to a temperature of approximately –85 degrees Celsius. The cooling of the cryo-element, in turn, freezes and cools the liquid in the balloon to a temperature of approximately –85 degrees Celsius. The resulting "ice ball" extracts heat from surrounding tissue resulting in the cryoablation of a substantially circumferential portion of tissue.

The system can also include a subsystem for directing energy into the "ice ball" to quickly thaw the frozen "ice ball" and restore blood flow through the affected conduit (e.g. pulmonary vein). Once the "ice ball" is thawed, the saline solution can be removed from the balloon and the balloon withdrawn from the patient's body. In one embodiment of the present invention, a radiofrequency (rf) antenna is mounted on either the first or cryo-catheter to thaw the "ice ball" and facilitate removal of the balloon from the patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
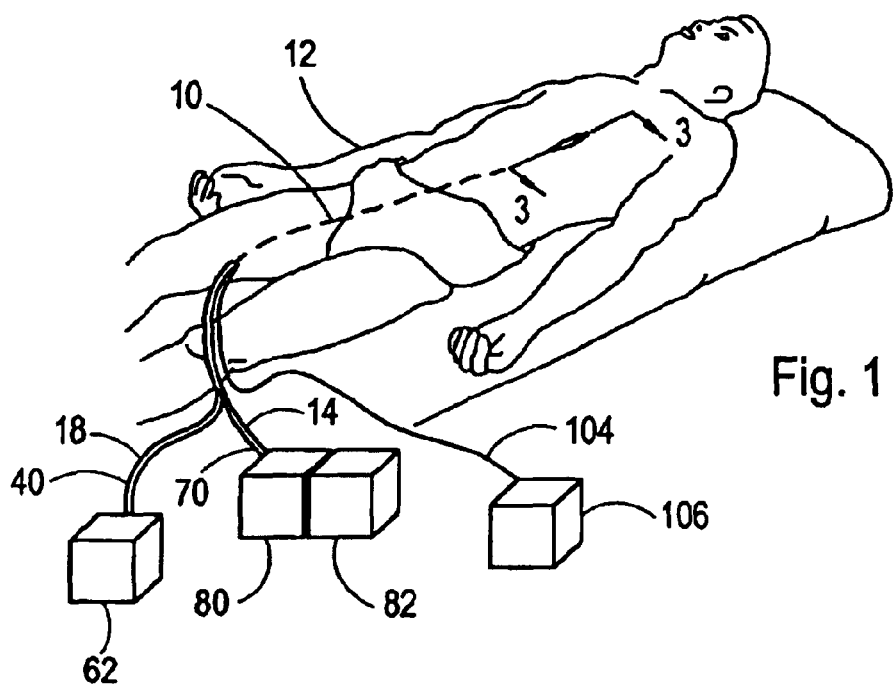
FIG. 1 is a perspective view of a system for ablating internal target tissue shown with the distal end of the system positioned at a treatment site in a patient and with peripheral components of the system shown schematically.

Referring initially to FIG. 1, a system 10 for cryoablating internal target tissue of a patient 12 is shown. As shown, the system 10 includes a balloon catheter 14 for positioning a balloon 16 (see FIG. 2) and a cryo-catheter 18 for positioning a cryo-element 20 at an internal treatment site of the patient 12. As further shown in FIG. 1, both the balloon catheter 14 and cryo-catheter 18 can be inserted into a peripheral artery of the patient 12 such as the femoral artery and advanced through the vasculature to a position in the upper body of the patient 12.

Figure 2:
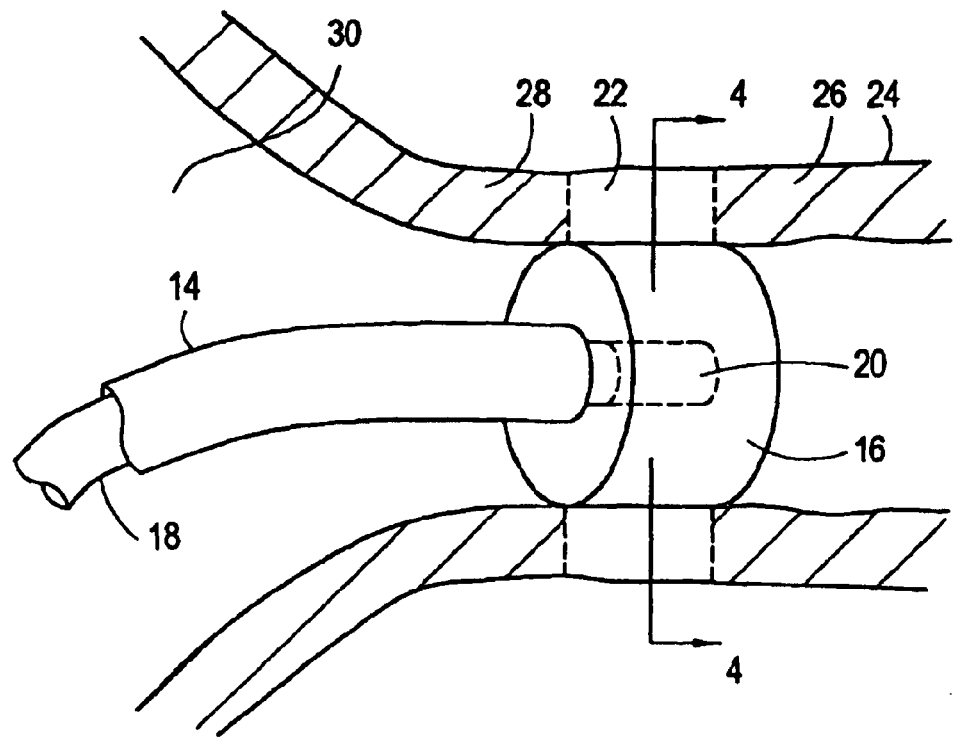
FIG. 2 is a perspective view of the distal end of a system for ablating internal target tissue shown positioned in a pulmonary vein.

Referring now to FIG. 2, an application of the system 10 is shown wherein a substantially circumferentially shaped target tissue 22 is ablated surrounding the ostium of a pulmonary vein 24. The resulting lesion, which can extend through the wall of the pulmonary vein 24 and into the tissue as shown, can function as a conduction block to prevent the transmission of electrical signals. In greater detail, the lesion can prevent electrical signals traveling toward the target tissue 22 from exemplary area 26 of the pulmonary vein 24 from passing through the ablated target tissue 22 to exemplary area 28. By preventing the transmission of these electrical signals, the ablated target tissue 22 can be used to treat heart ,arrhythmias such as atrial fibrillation. FIG. 2 further shows that the distal end of the system 10 can be passed through the left atrium 30 to access the pulmonary vein 24 and ablate the target tissue 22.

Figure 3:
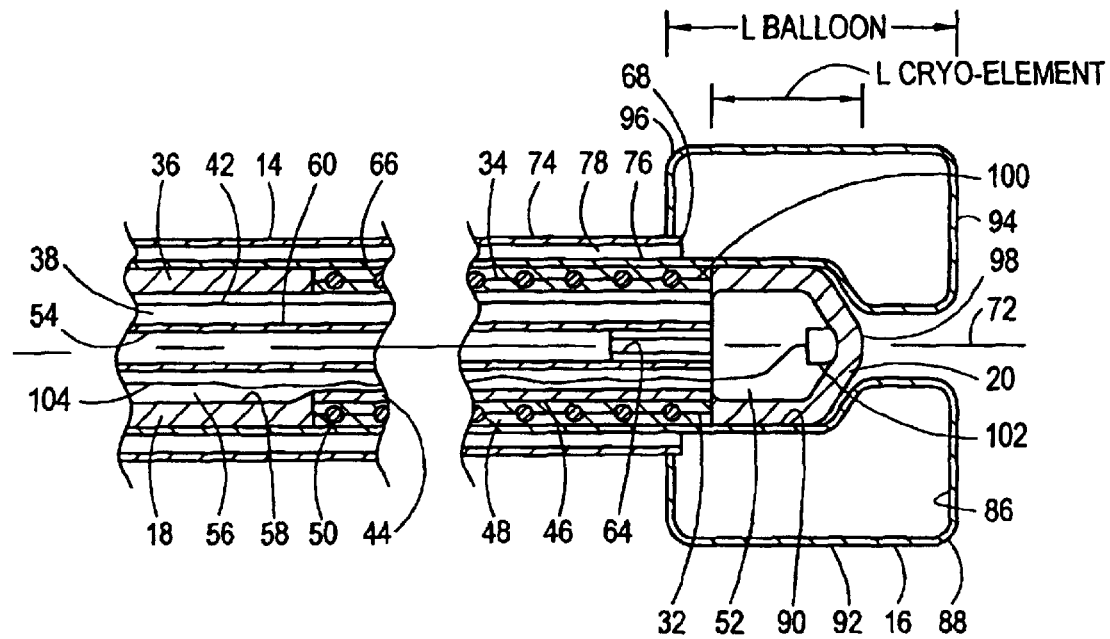
FIG. 3 is a sectional view of the distal end of the system shown in FIG. 2 as seen along line 3—3 in FIG. 1.

With reference now to FIG. 3, it can be seen that the cryo-element 20 is mounted on the cryo-catheter 18 at the distal end 32 of the cryo-catheter 18. As further shown, the cryo-catheter 18 is tubular-shaped and can include an articulation segment 34 and proximal shaft 36 that together establish a continuous lumen 38 that extends from the proximal end 40 (see FIG. 1) to the distal end 32 of the cryo-catheter 18. A suitable articulation segment 34 for use in the cryo-catheter 18 is disclosed in co-pending U.S. patent application Ser. No. 10/210,616, entitled "Nire Reinforced Articulation Segment" and filed on Jul. 31, 2002, which is assigned to the same assignee as the present invention. Co-pending U.S. application Ser. No. 10/210,616 is Incorporated by reference herein. Also shown in FIG. 3, the cryo-element 20 is formed with an expansion chamber 52 that is placed in fluid communication with the lumen 38 of the cryo-catheter 18.

In greater detail, the articulation segment 34 includes a control wire 42 that extends through the lumen 38 from an extracorporeal control mechanism (not shown) to the cryo-element 20. Additionally, FIG. 3 shows that a spine 44 is positioned between the cryo-element 20 and the proximal shaft 36. It can be further seen that the articulation segment 34 includes an Inner wall 46, an outer wall 48, and a helical spring 50 that is embedded between the inner wall 46 and the outer wall 48. Further, this assembly (i.e. the helical spring 50, inner wall 46 and outer wall 48) establishes a flexural modulus that is typically less than the modulus of the spine 44. Due to the difference in the respective flexural moduli of the assembly (i.e. the helical spring 50, inner wall 46 and outer wall 48) and the spine 44, whenever the control wire 42 is pulled, the cryo-element 20 can be predictably deflected through an arc in a predetermined plane for the purposes of steering and configuring the cryo-catheter 18 in the vasculature and heart of a patient 12.

Continuing with FIG. 3, the cryo-catheter 18 can further include a supply tube 54 that is positioned inside the lumen 38 of the cryo-catheter 18. It can be further seen that the supply tube 54 is positioned inside the lumen 38 of the cryo-catheter 18 to establish a return line 56 between the inner surface 58 of the cryo-catheter 18 and the outer surface 60 of the supply tube 54. For the system 10, the supply tube 54 can extend from the proximal end 40 of the cryo-catheter 18 to the distal end 32 of the cryo-catheter 18.

With cross reference now to FIGS. 1 and 3, it can be seen that system 10 further includes a refrigerant supply unit 62 that is positioned at an extracorporeal location to introduce a fluid refrigerant into the supply tube 54 at the proximal end 40 of the cryo-catheter 18. The fluid refrigerant then traverses through the supply tube 54 and enters the expansion chamber 52 of the cryo-element 20. As shown in FIG. 3, a flow restricting device 64, such as a capillary tube, can be inserted in the supply tube 54 at the distal end 32 of the cryo-catheter 18. With this cooperation of structure, the fluid refrigerant from the supply tube 54, passes through the flow restricting device 64 and then expands into the chamber 52 to cool the cryo-element 20.

In one embodiment of the present invention, a fluid refrigerant Is used that transitions from a liquid state to a gaseous state as it expands into the expansion chamber 52 of the cryo-element 20. A suitable refrigerant supply unit 62 for delivering a refrigerant in a liquid state to the distal end 32 of the cryo-catheter 18 for transition to a gaseous state in the expansion chamber 52 is disclosed in co-pending U.S. patent application Ser. No. 10/243,997, entitled "A Refrigeration Source for a Cryoablation Catheter" and filed on Sep. 12, 2002, which is assigned to the same assignee as the present invention. Co-pending U.S. application Ser. No. 10/243,997 is incorporated by reference herein. Heat absorbed by the refrigerant during this phase transition (i.e. latent heat) cools the cryo-element 20. After expansion, the gaseous fluid refrigerant passes through the return line 56 and exits the patient 12 at the proximal end 40 of the cryo-catheter 18. In one implementation, nitrous oxide is used as the refrigerant with suction applied to the return line 56 allowing the cryo-element 20 to be cooled to a temperature of approximately −85 degrees Celsius.

Figure 4:
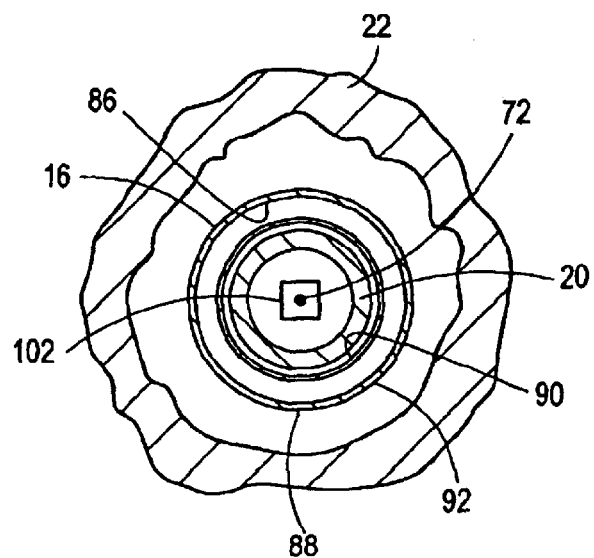
FIG. 4 is a sectional view of the distal end of the system shown in FIG. 2 as seen along line 4—4 in FIG. 2 showing the balloon in the collapsed configuration.
Figure 5:
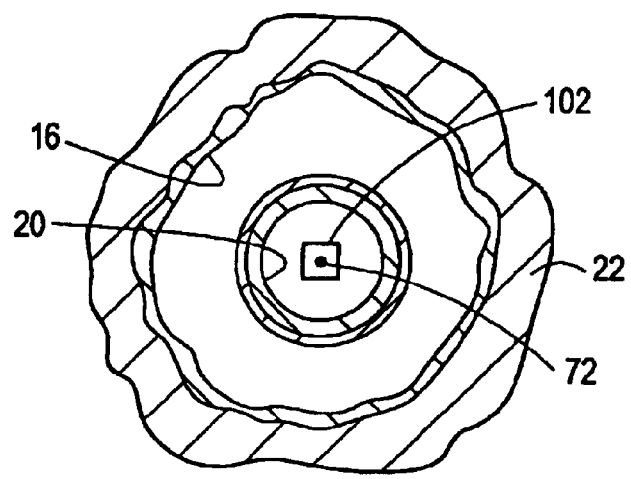
FIG. 5 is a sectional view as In FIG. 4 showing the balloon in the expanded configuration.

With cross-reference now to FIGS. 3–5, it can be seen that the system 10 includes a balloon 16 that can be configured in a collapsed configuration (see FIG. 4) to allow the collapsed balloon 16 to be advanced through the vasculature of the patient 12. It should be noted that the balloon 16 may alternatively be a so-called "free blown" balloon which is made of an elastomeric material that expands under pressure.

While the balloon 16 is in the collapsed configuration, the balloon catheter 14 can be used to interpose the collapsed balloon 16 between the cryo-element 20 and the target tissue 22. As best seen in FIG. 3, the balloon catheter 14 is formed with a lumen 66 that extends between the distal end 68 (see FIG. 1) of the balloon catheter 14 and proximal end 70 of the balloon catheter 14 As further shown, the cryo-catheter 18 is disposed in the lumen 66 of the balloon catheter 14 and the balloon catheter 14 and cryo-catheter 18 are arranged co-axially about longitudinal axis 72. It can be further seen that the balloon catheter 14 can include a first tube 74 and second tube 76 that together establish a liquid transfer lumen 78. The balloon 16 is attached to the distal end 68 of the balloon catheter 14 and placed in fluid communication with the liquid transfer lumen 78 of the balloon catheter 14. With this combination of structure, a pump 80 (see FIG. 1) can be used to introduce saline solution from a reservoir 82 into the proximal end 70 of the balloon catheter 14 for delivery to the balloon 16 to reconfigure the balloon 16 from a collapsed configuration (see FIG. 4) into an expanded configuration (see FIG. 5).

With cross-reference now to FIGS. 3 and 4, it can be seen that the balloon 16 has a substantially annular shaped cross-section in a plane substantially orthogonal to the axis 72. This shape allows the balloon 16, when expanded (see FIG. 5) to surround the cryo-element 20 and transfer heat from the target tissue 22 to the cryo-element 20 along substantially radial paths. As shown in FIGS. 3 and 4, the balloon 16 has an interior surface 86 for contacting the saline solution and an exterior surface 88. Also shown, the exterior surface 88 is formed with an inner surface portion 90 for surrounding and contacting said cryo-element 20 and an outer surface portion 92 for contacting a substantially circumferential shaped target tissue 22.

As best seen in FIG. 3, the balloon 16 extends from a distal end 94 to a proximal end 96 and defines a balloon length, $L_{balloon}$ therebetween. Further, the cryo-element 20 extends from a distal end 98 to a proximal end 100 and defines a cryo-element length, $L_{cryo-element}$ therebetween. FIG. 3 further shows that the balloon 16 can have a balloon length that is longer than the cryo-element length ($L_{balloon} > L_{cryo-element}$) to allow the expanded balloon 16 to surround the cryo-element 20 at the distal end 98 and proximal end 100 of the cryo-element 20.

With cross-reference to FIGS. 1 and 3, it can be seen that the system 10 also includes a radiofrequency (RF) antenna 102, which can be used to generate heat to quickly thaw frozen saline solution and restore blood flow through the affected conduit (e.g. pulmonary vein 24). As shown, the RF antenna 102 is electrically connected via wire 104 to signal generator 106 that is positioned at an extracorporeal location. Although the RF antenna 102 is shown positioned in the expansion chamber 52, it is to be appreciated that the RF antenna 102 could be positioned at other locations on the system 10. Also, it is to be appreciated by those skilled in the art that other sub-systems such as an RF electrode (not shown) for passing a current to a return electrode (also not shown) or an ultrasonic transducer (also not shown) could be used in place of the RF antenna 102 to thaw frozen saline.

The operation of the system 10 can best be appreciated with initial reference to FIGS. 1–3. First, the cryo-element 20 and distal end 32 of the cryo-catheter 18 are inserted into the vasculature of the patient 12, for example using a peripheral artery, and advanced passed the target tissue 22. As discussed above, for ablation of tissue surrounding the ostium of the pulmonary vein 24, the cryo-element 20 can be passed through the left atrium 30 of the patient's heart and into the pulmonary vein 24. The articulation segment 34 can be selectively manipulated during advancement of the cryo-element 20 to steer the cryo-element 20 through the vasculature and place the cryo-element 20 at the treatment site. With the cryo-element 20 In place, the balloon 16 is collapsed and then the balloon catheter 14 is used to advance the annular shaped balloon 16 over the cryo-catheter 18 to the treatment site. At the treatment site, the annular shaped balloon 16 is advanced over the cryo-element 20 to interpose the balloon 16 between the cryo-element 20 and the target tissue 22, as shown in FIG. 4.

With cross-reference now to FIGS. 4 and 5, it can be seen that with the collapsed balloon 16 interposed between the cryo-element 20 and the target tissue 22, pump 80 (shown in FIG. 1) can be activated to introduce saline solution into the balloon 16 to cause the balloon 16 to expand (expanded balloon shown in FIG. 5) and contact both the cryo-element 20 and the surrounding target tissue 22. As shown in FIG. 5, the shape of the balloon 16 (i.e. the annular shape) allows the balloon 16 to surround the cryo-element 20 and provide a large contact area between the balloon 16 and the cryo-element 20. The large contact area, in turn, provides for good heat transfer between the saline solution in the balloon 16 and the cryo-element 20. Additionally, the expanded balloon 16 functions to anchor the cryo-element 20 in place at the site of the target tissue 22.

Cross-referencing now to FIGS. 1 and 3, after the balloon 16 has been adequately filled with saline solution, the refrigerant supply unit 62 is activated to introduce a fluid refrigerant into the expansion chamber 52 of the cryo-element 20 and thereby cool the cryo-element 20. As indicated above, in one implementation of the system 10, nitrous oxide is used as the refrigerant allowing the cryo-element 20 to be cooled to a temperature of approximately −85 degrees Celsius. The cooling of the cryo-element 20, in turn, freezes and cools the saline solution in the balloon 16 to a temperature of approximately −85 degrees Celsius. This cooling can result in the formation of an "ice ball" that includes the frozen saline solution and can include frozen blood in the pulmonary vein 24. The "ice ball" extracts heat from target tissue 22 resulting in the cryoablation of a substantially circumferential portion of target tissue 22.

After the target tissue 22 has been successfully cryoablated, the signal generator 106 can be activated to generate heat via RF antenna 102 to quickly thaw the frozen "ice ball" and restore blood flow through the affected conduit (e.g. pulmonary vein 24). Once the "ice ball" is thawed, the saline solution can be removed from the balloon 16 and the system 10 withdrawn from the patient's body or moved to another treatment site, such as another pulmonary vein, for further cryoablation.

Figure 6:
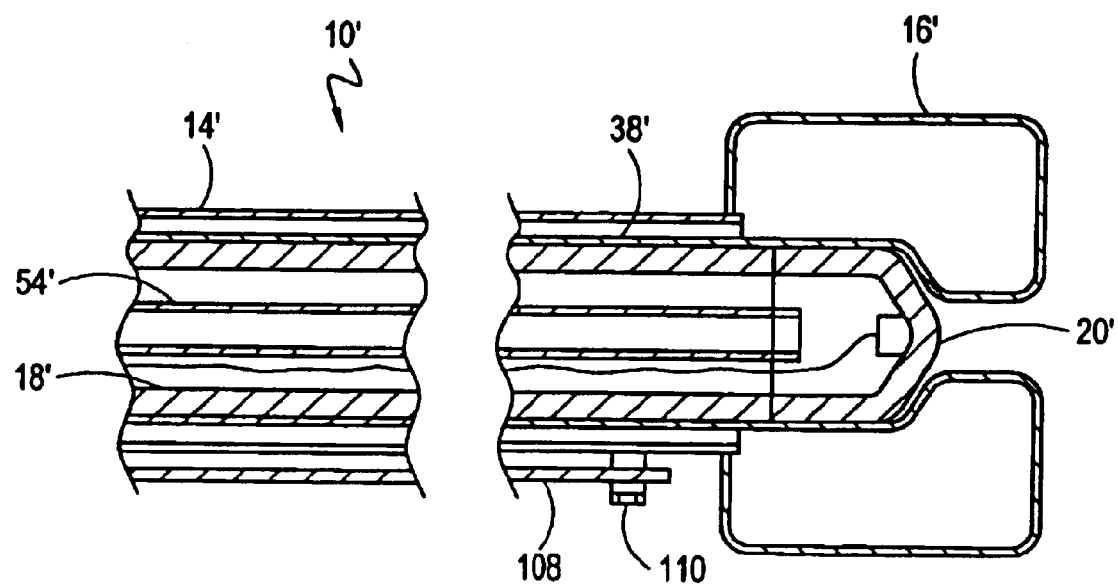
FIG. 6 is a sectional view as in FIG. 3 showing another embodiment of a system for ablating internal target tissue wherein a guidewire is used to guide the cryo-element and balloon to the treatment site.

FIG. 6 shows the distal end of another embodiment (designated system 10') for cryoablating internal target tissue wherein a guidewire 108 is used to position the cryo-element 20' and balloon 16' at the treatment site. As shown, an eyelet 110 is mounted on the balloon catheter 14' to allow the balloon catheter 14' to follow the guidewire 108. To place the distal end of the system 10' at the treatment site, the distal tip of the guidewire 108 is first inserted into the vasculature of the patient 12, for example using a peripheral artery, and advanced past the target tissue 22. For ablation of tissue surrounding the ostium of the pulmonary vein 24, the guidewire 108 can be passed through the left atrium 30 of the patient's heart and into the pulmonary vein 24. Once the guidewire 108 is in place, the eyelet 110 is threaded onto the guidewire 108. With the cryo-catheter 18'(including the supply tube 54') disposed in the lumen 38' of the balloon catheter 14', the cryo-element 20' and balloon 16' are advanced within the vasculature following the guidewire 108 until the cryo-element 20' and balloon 16' are positioned at the treatment site. At the treatment site, the position of the balloon 16' relative to the cryo-element can be adjusted by moving the balloon catheter 14' relative to the cryo-catheter 18'. With the cryo-element 20' and balloon 16' in place, the procedures described above with reference to the system 10 can be used to fill the balloon 16' with saline solution and cool the cryo-element 20' to ablate the target tissue.

While the particular Coaxial Catheter System for Performing a Single Step Cryoablation as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A system for cryoablating target tissue of a patient at a treatment site, said system comprising:

a cryo-element;

a balloon;

an assembly having a first catheter surrounding a lumen and a second catheter disposed in said lumen of said first catheter and moveable relative to said first catheter, said second catheter for positioning said cryo-element at the treatment site and said first catheter for interposing said balloon between said cryo-element and the target tissue;

means for introducing a liquid into said balloon to expand said balloon into contact with said cryo-element and the target tissue; and means for cooling said cryo-element to freeze said liquid and cryoablate the target tissue.

2. A system as recited in claim 1 wherein said first tube is elongated and defines a longitudinal axis and said second tube is disposed in said lumen of said first catheter and substantially centered on said longitudinal axis.

3. A system as recited in claim 1 wherein said balloon is substantially annularly shaped having an interior surface for contacting said liquid and an exterior surface formed with an inner surface portion for surrounding and contacting said cryo-element and an outer surface portion for contacting a substantially circumferential shaped target tissue.

4. A system as recited in claim 1 wherein said balloon has a distal end and a proximal end and defines a balloon length, $L_{balloon}$ therebetween, said cryo-element has a distal end and a proximal end and defines a cryo-element length, $L_{cryo-element}$ therebetween and wherein said balloon length is longer than said cryo-element length ($L_{balloon} > L_{cryo-element}$) to allow said balloon to surround said cryo-element.

5. A system as recited in claim 1 wherein said cryo-element is formed with an expansion chamber to allow a fluid to expand therein and cool said cryo-element.

6. A system as recited in claim 1 wherein said liquid comprises a saline solution.

7. A system as recited in claim 1 further comprising a radiofrequency antenna positioned on one of said first and second catheters to thaw said frozen liquid after cryoablation of the target tissue to allow for removal of said balloon from the patient.

8. A system as recited in claim 1 wherein said second catheter comprises a proximal catheter shaft having a distal end and an articulation segment mounted on said proximal catheter shaft at said distal end of said proximal catheter shaft.

9. A system for cryoablating target tissue of a patient at a treatment site, said system comprising:
   a cryo-element formed with a chamber;
   a balloon;
   an assembly having a first catheter surrounding a lumen and a second catheter disposed in said lumen of said first catheter and moveable relative to said first catheter, said second catheter for positioning said cryo-element at the treatment site and said first catheter for interposing said balloon between said cry element and the target tissue;
   a liquid reservoir;
   a pump in fluid communication with said reservoir and said balloon, said pump for transferring liquid from said reservoir to said balloon to expand said balloon into contact with said cryo-element and said target tissue; and
   a refrigerant supply unit for delivering a refrigerant to said cryo-element for expansion of said refrigerant in said chamber to freeze said liquid and cryoablate the target tissue.

10. A system as recited in claim 9 wherein said balloon is substantially annularly shaped having an interior surface for contacting said liquid and an exterior surface formed with an inner surface portion for surrounding and contacting said cryo-element and an outer surface portion for contacting a substantially circumferential shaped target tissue.

11. A system as recited in claim 9 wherein said first and second tubes are arranged co-axially.

12. A system as recited in claim 9 wherein said balloon has a distal end and a proximal end and defines a balloon length, $L_{balloon}$ therebetween, said cryo-element has a distal end and a proximal end and defines a cryo-element length, $L_{cryo-element}$ therebetween and wherein said balloon length is longer than said cryo-element length ($L_{balloon} > L_{cryo-element}$) to allow said balloon to surround said cryo-element.

13. A system as recited in claim 9 further comprising a radiofrequency antenna positioned on one of said first and second catheters to thaw said frozen liquid after cryoablation of the target tissue to allow for removal of said balloon from the patient.

14. A system as recited in claim 9 wherein said second catheter comprises a supply tube for transferring refrigerant from said refrigerant supply unit to said cryo-element.

15. A method for cryoablating target tissue of a patient, said method comprising the steps of:
   positioning a cryo-element proximate the target tissue;
   providing an annular shaped balloon having an exterior surface formed with an inner surface portion and an outer surface portion;
   interposing said balloon between said cryo-element and said target tissue;
   filling said balloon with a liquid to contact said cryo-element with said inner surface portion of said balloon and said target tissue with said outer surface portion of said balloon; and
   cooling said cryo-element to freeze said liquid and cryoablate the target tissue.

16. A method as recited in claim 15 wherein the target tissue has a substantially circumferential shape.

17. A method as recited in claim 15 wherein said cryo-element comprises an expansion chamber and wherein said method further comprises the step of delivering a refrigerant from an extracorporeal location to said cryo-element for expansion in said chamber to cool said cryo-element.

18. A method as recited in claim 15 wherein said step of filling said balloon with a liquid is accomplished by pumping a saline solution from an extracorporeal location into said balloon.

19. A method as recited in claim 15 wherein said method further comprises the steps of:
   providing a first catheter surrounding a lumen;
   disposing a second catheter in said lumen of said first catheter;
   attaching said cryo-element to said second catheter, and
   attaching said balloon to said first catheter.

20. A method as recited in claim 15 wherein said balloon has a distal end and a proximal end and defines a balloon length, $L_{balloon}$ therebetween, said cryo-element has a distal end and a proximal end and defines a cryo-element length, $L_{cryo-element}$ therebetween and wherein said balloon length is longer than said cryo-element length ($L_{balloon} > L_{cryo-element}$) to allow said balloon to surround said cryo-element.

* * * * *

UNITED STATES PATENT AND TRADEMARK OFFICE
CERTIFICATE OF CORRECTION

PATENT NO. : 6,796,979 B2
DATED : September 28, 2004
INVENTOR(S) : David J. Lentz It is certified that error appears in the above-identified patent and that said Letters Patent is hereby corrected as shown below:

Column 4,
Line 63, delete ""Nire" insert -- "Wire --

Column 9,
Line 18, delete "cry element" insert -- cryo-element --

Signed and Sealed this

Fifth Day of April, 2005

JON W. DUDAS
*Director of the United States Patent and Trademark Office*